(12) United States Patent
Okamura

(10) Patent No.: US 7,810,997 B2
(45) Date of Patent: Oct. 12, 2010

(54) RADIOGRAPHIC APPARATUS AND RADIATION DETECTION SIGNAL PROCESSING METHOD

(75) Inventor: Shoichi Okamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 332 days.

(21) Appl. No.: 12/064,200

(22) PCT Filed: Aug. 31, 2005

(86) PCT No.: PCT/JP2005/015895

§ 371 (c)(1),
(2), (4) Date: Feb. 19, 2008

(87) PCT Pub. No.: WO2007/026419

PCT Pub. Date: Mar. 8, 2007

(65) Prior Publication Data

US 2009/0147921 A1   Jun. 11, 2009

(51) Int. Cl.
*G01D 18/00* (2006.01)
*H05G 1/64* (2006.01)
(52) U.S. Cl. .................. 378/207; 378/62; 378/98.8
(58) Field of Classification Search ............... 378/42, 378/62, 91, 98.8, 98.12, 190, 207
See application file for complete search history.

(56) References Cited

U.S. PATENT DOCUMENTS

| | | | | |
|---|---|---|---|---|
| 5,249,123 A | * | 9/1993 | Hsieh | 378/19 |
| 5,265,013 A | * | 11/1993 | King et al. | 378/4 |
| 5,331,682 A | * | 7/1994 | Hsieh | 378/19 |
| 5,359,638 A | * | 10/1994 | Hsieh et al. | 378/4 |
| 5,517,544 A | * | 5/1996 | Levinson | 378/4 |
| 5,644,610 A | * | 7/1997 | Crawford et al. | 378/19 |
| 5,923,722 A | * | 7/1999 | Schulz | 378/98.8 |
| 6,404,853 B1 | * | 6/2002 | Odogba et al. | 378/98.8 |
| 6,493,646 B1 | * | 12/2002 | Hsieh et al. | 702/104 |
| 6,600,159 B2 | * | 7/2003 | Overdick et al. | 250/370.11 |
| 6,621,887 B2 | * | 9/2003 | Albagli et al. | 378/42 |
| 6,798,864 B2 | * | 9/2004 | Petrick et al. | 378/98.8 |
| 6,949,746 B2 | * | 9/2005 | Stierstorfer | 250/336.1 |

(Continued)

FOREIGN PATENT DOCUMENTS

JP   09-009153 A   1/1997

(Continued)

OTHER PUBLICATIONS

International Search Report for the Application No. PCT/JP2005/015895, mailed Oct. 25, 2005.

*Primary Examiner*—Allen C. Ho
(74) *Attorney, Agent, or Firm*—Cheng Law Group, PLLC

(57) ABSTRACT

A radiographic apparatus according to this invention stores, before an imaging event, offset images and gain correcting images corresponding to a plurality of storage times, and acquires a lag image and a radiographic image based on these stored images. Then, lag correction is carried out to remove lags, using the lag image, from the radiographic image. In this way, from the radiographic image taking into consideration the offset images and gain correcting images corresponding to the storage times, lags are removed using the lag image which similarly fakes into consideration the offset images and gain correcting images corresponding to the storage times. Lag-behind parts, including offset and gain components, are removed from radiation detection signals in a simple way.

4 Claims, 9 Drawing Sheets

U.S. PATENT DOCUMENTS

| | | | |
|---|---|---|---|
| 7,065,177 B2 * | 6/2006 | Yanoff et al. | 378/98.12 |
| 7,208,717 B2 * | 4/2007 | Partain et al. | 250/214 C |
| 7,377,691 B2 * | 5/2008 | Okamura et al. | 378/207 |
| 7,428,294 B2 * | 9/2008 | Spahn | 378/62 |
| 7,570,735 B2 * | 8/2009 | Konno et al. | 378/19 |
| 7,573,038 B2 * | 8/2009 | Yokoyama et al. | 250/370.09 |

FOREIGN PATENT DOCUMENTS

| | | |
|---|---|---|
| JP | 2003-190126 A | 7/2003 |
| JP | 2004-242741 A | 9/2004 |
| JP | 2004-329932 A | 11/2004 |

* cited by examiner

Fig. 4

(a) offset non-irradiation time

| $O_{11}$ | $O_{12}$ |
|---|---|
| $O_{21}$ | $O_{22}$ |

O (b) offset irradiation time

| $O_{11}+S_{11}$ | $O_{12}+S_{12}$ |
|---|---|
| $O_{21}+S_{21}$ | $O_{22}+S_{22}$ |

(a) gain

| $S_{11}$ | $S_{12}$ |
|---|---|
| $S_{21}$ | $S_{22}$ |

S (b) gain

| $S_o$ | $S_o$ |
|---|---|
| $S_o$ | $S_o$ |

S

| | storage time | offset image | gain correcting image |
|---|---|---|---|
| corres. 1 | $\Delta T1$ | O1 | G1 |
| corres. 2 | $\Delta T2$ | O2 | G2 |
| corres. 3 | $\Delta T3$ | O3 | G3 |

RADIOGRAPHIC APPARATUS AND RADIATION DETECTION SIGNAL PROCESSING METHOD

TECHNICAL FIELD

This invention relates to a radiographic apparatus and a radiation detection signal processing method for obtaining radiographic images based on radiation detection signals resulting from radiation emitted to and transmitted through an object under examination. More particularly, the invention relates to a technique for eliminating lag-behind parts from the radiation detection signals.

BACKGROUND ART

An example of radiographic apparatus is an imaging apparatus that obtains X-ray images by detecting X rays. This apparatus used an image intensifier as an X-ray detecting device in the past. In recent years, a flat panel X-ray detector (hereinafter called simply "FPD") has come to be used instead.

The FPD has a sensitive film laminated on a substrate, detects radiation incident on the sensitive film, converts the detected radiation into electric charges, and stores the electric charges in capacitors arranged in a two-dimensional array. The electric charges are read by turning on switching elements, and are transmitted as radiation detection signals to an image processor. The image processor obtains an image having pixels based on the radiation detection signals.

The FPD is lightweight and free from complicated detecting distortions compared with the image intensifier used heretofore. Thus, the, FPD has advantages in terms of apparatus construction and image processing.

However, when the FPD is used, the X-ray detection signals include lag-behind parts. A lag-behind part results in an afterimage from X-ray irradiation in a preceding imaging event appearing as an artifact on a next X-ray image. Particularly, in a fluoroscopy that performs X-ray irradiation continually at short time intervals (e.g. $1/30$ second), time lags of the lag-behind parts have influences serious enough to hinder diagnosis.

Artifacts due to lag-behind parts are reduced by reducing long time constant components of the lag-behind parts by using backlight (see Patent Document 1, for example), or by regarding the lag-behind parts as a total of exponential functions having a plurality of time constants, and performing a lag correction by recursive computation using these exponential functions (see Patent Document 2, for example).

Where backlight is used as disclosed in the Patent Document 1 noted above, the construction becomes complicated by a construction required for backlight. Particularly where backlight is used in an FPD having a lightweight construction, the construction must become heavy and complicated again. In the case of Patent Document 2, the lag correction must be carried out by performing recursive computations the number of times X-ray detection signals are sampled. This renders the lag correction complicated and cumbersome.

In order to remove lag-behind parts included in X-ray detection, signals simply from the X ray detection signals, it is conceivable in performing a lag correction, to acquire a plurality of X-ray detection signals in time of non-irradiation before irradiation of X rays in an imaging event, acquire a lag image based on the X-ray detection signals, and using this image to remove the lags from a product X-ray image.

In addition to lag correction, correction processes include offset correction, gain correction, and defect correction, for example. To perform offset correction, for example, an offset image is obtained beforehand in time of non-irradiation. The above offset image is subtracted from an original image based on X-ray detection signals. An offset image is different for each mode such as storage time, amplification, factor (gain) of an amplifier or pixel binning (addition of a plurality of pixels). An offset image according to a mode is obtained to perform offset correction, (see Patent Document 3, for example). Pixel binning includes a 1×1 mode which outputs pixels in 1 to 1, a 2×2 mode which outputs four pixels of 2×2 in rows and columns to one pixel, and a 4×4 mode which outputs 16 pixels of 4×4 in rows and columns to one pixel.

[Patent Document 1]

Unexamined Patent Publication No. H9-9153 (pages 3-8, FIG. 1)

[Patent Document 2]

Unexamined Patent Publication No. 2004-242741 (pages 4-11, FIGS. 1 and 3-6)

[Patent Document 3]

Unexamined Patent Publication No. 2003-190126 (pages 3-6, FIG. 1)

DISCLOSURE OF THE INVENTION

Problems to be Solved by the Invention

However, there are the following problems with the technique of removing lags from a product X-ray image using the above acquired lag image. The X-ray detection signals acquired in time of non-irradiation include offset components due to dark current. With this technique, therefore, both offset, and lag components can be corrected simultaneously by removing lags, using a lag image including the offset components, from an uncorrected X-ray image immediately after image pick-up and not having undergone offset correction or gain correction.

In practice, however, the offset components (i.e. offset values) have a different property according to a storage time for accumulating signal information (electric charges). It is therefore necessary to subtract the offset values corresponding to the storage time used at an image pick-up time. In practice, the storage time used at an image pick-up time is dependent on a pulse width of X rays variable in time with a thickness and the like of an object under examination. It is impossible to determine the storage time at the time of image pick-up beforehand.

On the other hand, when collecting a plurality of X-ray detection signals in time of non-irradiation in order to acquire a lag image, the signals should be collected within a minimum storage time. Otherwise, the lag collection itself will consume a long time, which is undesirable. Thus, the collection for acquisition of a lag image and an actual image pick-up have to be performed for different storage times (different modes). This requires an improvement for enabling lag correction even for the different storage times. For gain correction also, it is necessary to use an image for gain correction according to different storage times.

This invention has been made having regard to the state of the art noted above, and its object is to provide a radiographic apparatus and a radiation detection signal processing method for eliminating lag-behind parts, including offset or gain components, from radiation detection signals in a simple way.

Means for Solving the Problem

To fulfill the above object, this invention employs the following construction.

A radiographic apparatus according to this invention is a radiographic apparatus for obtaining radiographic images based on radiation detection signals comprising a radiation emitting device for emitting radiation toward an object under examination; a radiation detecting device for detecting radiation transmitted through the object; an offset image storage device for storing offset images corresponding to a plurality of storage times for accumulating information on the signals, the offset images being used to perform offset correction for removing offset values superimposed on the signals; a non-irradiation signal, acquiring device for acquiring a plurality of radiation detection signals detected from the radiation detecting device in time of non-irradiation before irradiation of the radiation in an imaging event; a lag image acquiring device for acquiring a lag image based on the radiation detection signals acquired by the non-irradiation signal acquiring device, and the offset images stored in said offset image storage device and corresponding to the storage times for the non-irradiation signal acquiring device; an irradiation signal acquiring device for acquiring the radiation detection signals detected, from the radiation detecting device in time of irradiation of the radiation in the imaging event; a radiographic image acquiring device for acquiring a radiographic image serving an intended purpose based on the radiation detection signals acquired by the irradiation signal acquiring device, and the offset images stored in said offset image storage device and corresponding to the storage times for the irradiation signal acquiring device; and a lag correcting device for removing lags, using the lag image acquired by said lag image acquiring device, from the radiographic image acquired by the radiographic image acquiring device, thereby performing a lag correction of lag-behind parts by removing the lag-behind parts from the radiation detection signals.

According to the radiographic apparatus of this invention, offset images are used to carry out offset correction for removing offset values superimposed on signals. The offset images corresponding to a plurality of storage times for accumulating signal information are stored in the offset image storage device. The non-irradiation signal acquiring device acquires a plurality of radiation detection signals detected from the radiation detecting device in time of non-irradiation before irradiation of the radiation in an imaging event. Based on these radiation detection signals acquired by the non-irradiation signal acquiring device, the offset images stored in the above offset image storage device and corresponding to the storage times for the non-irradiation signal acquiring device, the lag image acquiring device acquires a lag image. On the other hand, the irradiation signal acquiring device acquires radiation detection, signals detected from the radiation detecting device in time of irradiation of the radiation in the imaging event. Based on the radiation detection signals acquired by the irradiation signal acquiring device, and the offset images stored in the above offset image storage device and corresponding to the storage times for the irradiation signal acquiring device, the radiographic image acquiring device acquires a radiographic image serving the intended purpose. The lag correcting device removes lags, using the lag image acquired by the lag image acquiring device, from the radiographic image acquired by the radiographic image acquiring device, thereby performing a lag correction of lag-behind parts by removing the lag-behind parts from the radiation detection, signals. Thus, there is no need to carry out lag correction by performing recursive computations the number of limes radiation detection signals are sampled, as described in Patent Document 2 noted hereinbefore. Further, the lag image forming the basis for the above lag correction, and the radiation image which is the target of the lag correction, take into consideration the offset images and lag correcting images corresponding to the respective storage times, it becomes possible to perform appropriately also offset correction according to the storage times by lag correction. A lag-behind part may therefore be eliminated from a radiation detection signal in a simple way. Further, there is no need to use backlight as used in Patent Document 1 noted hereinbefore. This avoids complication of the apparatus construction.

A different radiographic apparatus according to this invention is a radiographic apparatus for obtaining radiographic images based on radiation detection signals, comprising a radiation emitting device for emitting radiation toward an object under examination; a radiation detecting device for detecting radiation transmitted through the object; a gain correcting image storage device for storing gain correcting images corresponding to a plurality of storage times for accumulating information on the signals, the gain correcting images being used to perform gain correction for equalizing signal levels of pixels to be outputted; a non-irradiation signal acquiring device for acquiring a plurality of radiation detection signals detected from the radiation detecting device in time of non-irradiation before irradiation of the radiation in an imaging event; a lag image acquiring device for acquiring a lag image based on the radiation detection signals acquired by the non-irradiation signal acquiring device, and the gain correcting images stored in said gain correcting image storage device and corresponding to the storage times for the non-irradiation signal acquiring device; an irradiation signal acquiring device for acquiring the radiation detection signals detected from the radiation detecting device in time of irradiation of the radiation in the imaging event; a radiographic image acquiring device for acquiring a radiographic image serving an intended purpose based on the radiation detection signals acquired by the irradiation signal acquiring device, and the gain correcting images stored in said gain correcting image storage device and corresponding to the storage times for the irradiation signal acquiring device; and a lag correcting device for removing lags, using the lag image acquired by said lag image acquiring device, from the radiographic image acquired by the radiographic image acquiring device, thereby performing a lag correction of lag-behind parts by removing the lag-behind parts from the radiation detection signals.

According to the different radiographic apparatus of this invention, gain correcting images are used to carry out gain correction for equalizing signal levels of pixels to be outputted. The gain correcting images corresponding to a plurality of storage times for accumulating signal information are stored in the gain correcting image storage device. The non-irradiation signal acquiring device acquires a plurality of radiation detection signals detected from the radiation detecting device in time of non-irradiation before irradiation of the radiation in an imaging event. Based on these radiation detection signals acquired by the non-irradiation signal acquiring device, the gain correcting images stored in the above gain correcting image storage device and corresponding to the storage times for the non-irradiation signal acquiring device, the lag image acquiring device acquires a lag image. On the other hand, the irradiation signal acquiring device acquires radiation detection signals detected from the radiation detecting device in time of irradiation of the radiation in the imaging event. Based on the radiation detection signals acquired by the irradiation signal acquiring device, and the gain correcting images stored in the above gain correcting image storage device and corresponding to the storage times for the irradiation signal acquiring device, the radiographic image acquiring device acquires a radiographic image serving the intended purpose. The lag correcting device removes lags, using the lag image acquired by the lag image acquiring device, from the radiographic image acquired by the radiographic image acquiring device, thereby performing a lag correction of lag-behind parts by removing the lag-behind parts from the radiation detection signals. Thus, there is no need to carry out lag correction by performing recursive computations the number of times radiation detection signals are sampled, as described in Patent Document 2 noted hereinbefore. Further, the lag image forming the basis for the above lag correction, and the radiation image which is the target of the lag correction, take into consideration the gain correcting images and lag correcting images corresponding to the respective storage times. If becomes possible to perform appropriately also gain correction according to the storage times by lag correction, A lag-behind part may therefore be eliminated from a radiation detection signal in a simple way. Further, there is no need to use backlight as used in. Patent Document 1 noted hereinbefore. This avoids complication of the apparatus construction.

A radiation detection signal processing method according to this invention is a radiation detection signal processing method for performing a signal processing to obtain radiographic images based on radiation detection signals detected by irradiating an object under examination, said signal processing comprising an offset image storing step for storing, before an imaging event, offset images corresponding to a plurality of storage times for accumulating information on the signals, the offset images being used to perform offset correction for removing offset values superimposed on the signals; a non-irradiation signal acquiring step for acquiring a plurality of radiation detection signals in time of non-irradiation before irradiation of the radiation in the imaging event; a lag image acquiring step for acquiring a lag image based on the radiation detection signals acquired in the non-irradiation signal acquiring step, and the offset images stored in said offset image storage step and corresponding to the storage times in the non-irradiation signal acquiring step; an irradiation signal acquiring step for acquiring the radiation detection signals in time of irradiation of the radiation in the imaging event; a radiographic image acquiring step for acquiring a radiographic image serving an intended purpose based on the radiation detection signals acquired in the irradiation signal acquiring step, and the offset images stored in said offset, image storage step and corresponding to the storage times in the irradiation signal acquiring step; and a lag correcting step for removing lags, using the lag image acquired in said lag image acquiring step, from the radiographic image acquired in the radiographic image acquiring step, thereby performing a lag correction of lag-behind parts by removing the lag-behind parts from the radiation detection signals.

According to the radiation detection signal processing method of this invention, offset images are used to carry out offset correction for removing offset values superimposed on signals. The offset images corresponding to a plurality of storage times for accumulating signal information are stored in the offset image storing step before an imaging event. The non-irradiation signal acquiring step acquires a plurality of radiation detection signals in time of non-irradiation before irradiation of the radiation in the imaging event. Based on these radiation detection signals acquired in the non-irradiation signal acquiring step, the offset images stored in the above offset image storing step and corresponding to the storage times for the non-irradiation signal acquiring step, the lag image acquiring step acquires a lag image. On the other hand, the irradiation signal acquiring step acquires radiation detection signals in time of irradiation of the radiation in the imaging event. Based on the radiation detection signals acquired in the irradiation signal acquiring step, and the offset images stored in the above offset image storing step and corresponding to the storage times for the irradiation signal acquiring step, the radiographic image acquiring step acquires a radiographic image serving the intended purpose. The lag correcting step removes lags, using the lag image acquired in the lag image acquiring step, from the radiographic image acquired in the radiographic image acquiring step, thereby performing a lag correction of lag-behind parts by removing the lag-behind parts from the radiation detection signals. Thus, there is no need to carry out lag correction by performing recursive computations the number of times radiation detection signals are sampled, as described, in Patent Document 2 noted hereinbefore. Further, the lag image forming the basis for the above lag correction, and the radiation image which is the target of the lag correction, take into consideration the offset images and lag correcting images corresponding to the respective storage times. It becomes possible to perform appropriately also offset correction according to the storage times by lag correction. A lag-behind part may therefore be eliminated from a radiation detection signal in a simple way.

A different radiation detection signal processing method according to this invention is a radiation detection signal processing method for performing a signal processing to obtain radiographic images based on radiation detection signals detected by irradiating an object under examination, said signal processing comprising a gain correcting image storing step for storing, before an imaging event, gain correcting images corresponding to a plurality of storage times for accumulating information on the signals, the gain correcting images being used to perform gain correction for equalizing signal levels of pixels to be outputted; a non-irradiation signal acquiring step for acquiring a plurality of radiation detection signals in time of non-irradiation before irradiation of the radiation in the imaging event; a lag image acquiring step for acquiring a lag image based on the radiation detection signals acquired in the non-irradiation signal acquiring step, and the gain correcting images stored in said gain correcting image storage step and corresponding to the storage times in the non-irradiation signal acquiring step; an irradiation signal acquiring step for acquiring the radiation detection signals in time of irradiation of the radiation in the imaging event; a radiographic image acquiring step for acquiring a radiographic image serving an intended purpose based on the radiation detection signals acquired in the irradiation signal acquiring step, and the gain correcting images stored in said gain correcting image storage step and corresponding to the storage times in the irradiation signal acquiring step; and a lag correcting step for removing lags, using the lag image acquired in said lag image acquiring step, from the radiographic image acquired in the radiographic image acquiring step, thereby performing a lag correction of lag-behind parts by removing the lag-behind parts from the radiation detection signals.

According to the different radiation detection signal processing method of this invention, gain correcting images are used to carry out gain, correction for equalizing signal levels of pixels to be outputted. The gain correcting images corresponding to a plurality of storage times for accumulating signal information are stored in the gain correcting image storing step before an imaging event. The near irradiation signal acquiring step acquires a plurality of radiation detection, signals in time of non-irradiation, before irradiation of the radiation in the imaging event. Based on these radiation detection signals acquired, in the non-irradiation signal acquiring step, the gain correcting images stored in the above gain correcting image storing step and corresponding to the storage times for the non-irradiation signal acquiring step, the lag image acquiring step acquires a lag image. On the other hand, the irradiation signal acquiring step acquires radiation detection signals in time of irradiation of the radiation in the imaging event. Based on the radiation detection signals acquired in the irradiation signal acquiring step, and the gain, correcting images stored in the above gain correcting image storing step and corresponding to the storage times for the irradiation signal acquiring step, the radiographic image acquiring step acquires a radiographic image serving the intended purpose. The lag correcting step removes lags, using the lag image acquired in the lag image acquiring step, from the radiographic image acquired in the radiographic image acquiring step, thereby performing a lag correction of lag-behind parts by removing the lag-behind parts from the radiation detection signals. Thus, there is no need to carry out lag correction by performing recursive computations the number of times radiation detection signals are sampled, as described in Patent Document 2 noted hereinbefore. Further, the lag image forming the basis for the above lag correction, and the radiation image which is the target of the lag correction, take into consideration the gain correcting images and lag correcting images corresponding to the respective storage times. It becomes possible to perform appropriately also gain correction according to the storage times by lag correction. A lag-behind part may therefore be eliminated from a radiation detection signal in a simple way.

EFFECTS OF THE INVENTION

With the radiographic apparatus and radiation detection, signal processing method, according to this invention, from a radiographic image taking into consideration offset images and gain correcting images corresponding to storage times, lags are removed using a lag image which similarly takes into consideration the offset images and gain correcting images corresponding to the storage times. Thus, lag-behind parts, including offset and gain components, included in radiation detection signals are removed from the radiation detection signals in a simple way.

BRIEF DESCRIPTION OF THE DRAWINGS

[FIGS. 4](a) and (b) are explanatory views schematically showing offset correction.

[FIG. 5](a) and (b) are explanatory views schematically showing gain correction.

DESCRIPTION OF REFERENCES

Figure 1:
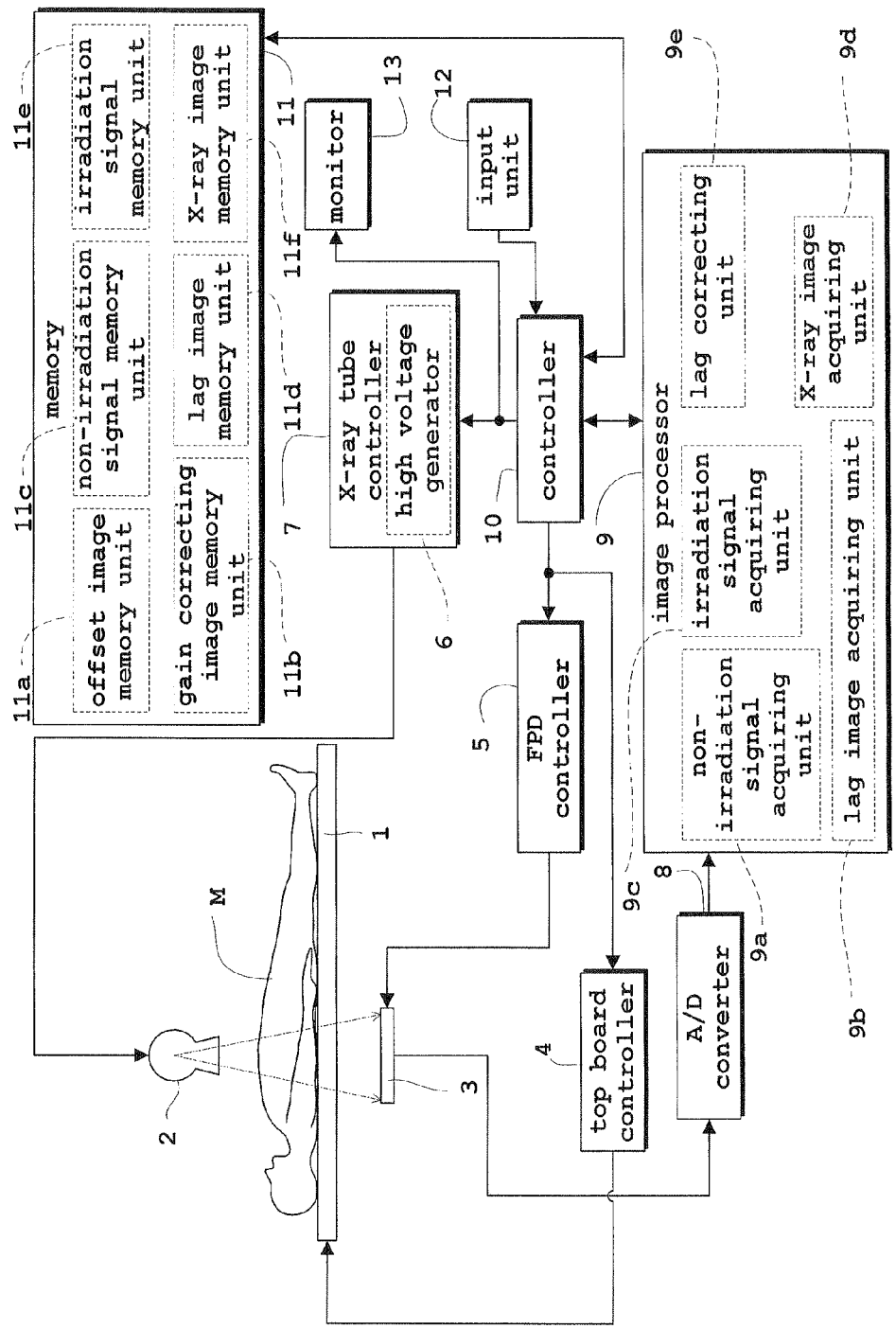
[FIG. 1]Block diagram of a fluoroscopic apparatus according to the invention.

2 . . . X-ray tube
3 . . . flat panel X-ray detector (FPD)
9a . . . non-irradiation signal acquiring unit
9b . . . lag image acquiring unit
9c . . . irradiation signal acquiring unit
9d . . . X-ray image acquiring unit
9e . . . lag correcting unit
11a . . . offset image memory unit
11b . . . gain correcting image memory unit
X, X', Y . . . X-ray image
L, L'. . . lag image
M . . . patient

BEST MODE FOR CARRYING OUT THE INVENTION

In a radiation detection signal processing method, offset images and gain correcting images corresponding to a plurality of storage times are stored in memory before an imaging event, and a lag image is acquired and a radiographic image is acquired based on these stored images. Lag correction is carried out by removing lags, using the lag image, from the radiographic image. From the radiographic image taking into consideration the offset images and gain correcting images corresponding to the storage times, lags are removed using the lag image which similarly takes into consideration the offset images and gain correcting images corresponding to the storage times. Thus, the object of eliminating lag-behind parts, including offset and gain components, from radiation detection signals in a simple way has been fulfilled.

Embodiment 1

Figure 2:
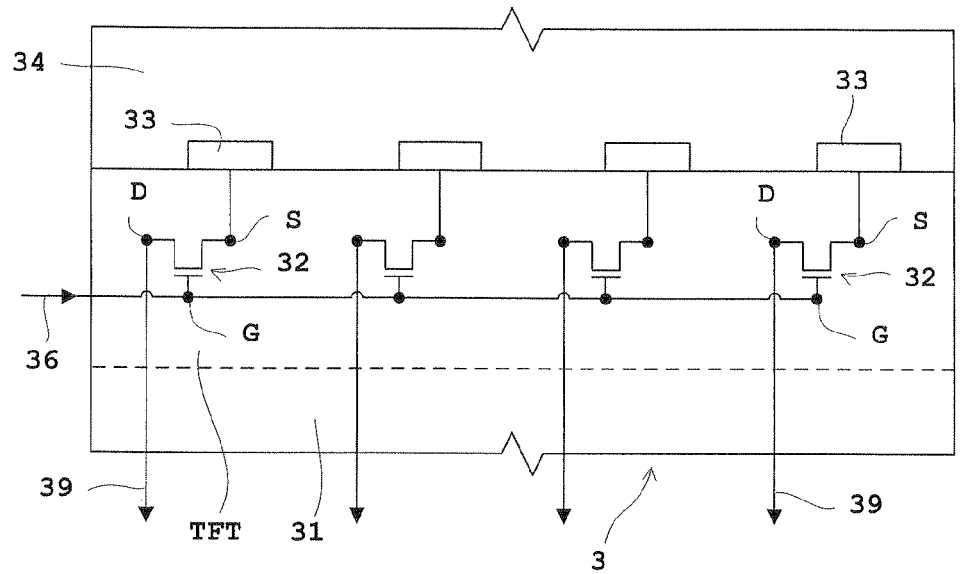
[FIG. 2]Equivalent circuit, seen in side view, of a flat panel X-ray detector used in the fluoroscopic apparatus.
Figure 3:
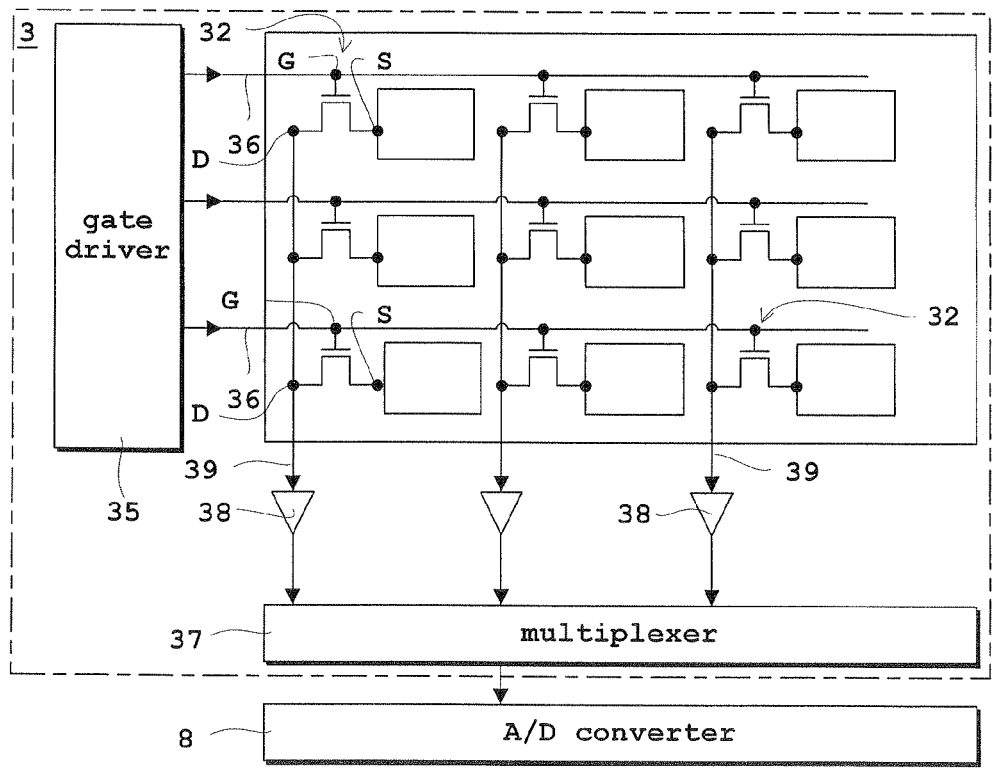
[FIG. 3]Equivalent circuit, seen in plan view, of the flat panel X-ray detector.

Embodiment 1 of this invention will be described hereinafter with reference to the drawings. FIG. 1 is a block diagram of a fluoroscopic apparatus in Embodiment 1. FIG. 2 is an equivalent circuit, seen in side view, of a flat panel X-ray detector used in the fluoroscopic apparatus. FIG. 3 is an equivalent circuit, seen in plan view, of the flat panel X-ray detector. Embodiment 1, and also Embodiments 2 and 3 to follow, will be described, taking the flat panel X-ray detector (hereinafter called "FPD" as appropriate) as an example of radiation detection device, and the fluoroscopic apparatus as an example of radiographic apparatus.

As shown in FIG. 1, the fluoroscopic apparatus in Embodiment 1 includes a top board 1 for supporting a patient M, an X-ray tube 2 for emitting X rays toward the patient M, and an FPD 3 for detecting X rays transmitted through the patient M. The X-ray tube 2 corresponds to the radiation emitting device in this invention. The FPD 3 corresponds to the radiation detecting device in this invention.

The fluoroscopic apparatus further includes a top hoard controller 4 for controlling vertical and horizontal movements of the top board 1, an FPD controller 5 for controlling scanning action of the FPD 3, an X-ray tube controller 7 having a high voltage generator 6 for generating a tube voltage and tube current for the X-ray tube 2, an analog-to-digital converter 8 for fetching charge signals from the FPD 3 and digitizing the charge signals into X-ray detection signals, an image processor 9 for performs various processes based on the X-ray detection signals outputted from the analog-to-digital converter 8, a controller 10 for performing an overall control of these components, a memory 11 for storing processed images, an input unit 12 for the operator to input, various settings, and a monitor 13 for displaying the processed images and other information.

The top board controller 4 controls movements of the top board 1, such as moving the top board 1 horizontally to place the patient M in an imaging position, vertically moving and/or rotating the top board 1 to set the patient M to a desired position, horizontally moving the top board 1 during an imaging operation, and horizontally moving the top board 1 to withdraw the patient M from the imaging position after the imaging operation. The FPD controller 5 controls scanning action by moving the FPD 3 horizontally or revolving the FPD 3 about the body axis of patient M. The high voltage generator 8 generates the tube voltage and tube current for the X-ray tube 2, to emit X rays. The X-ray tube controller 7 controls scanning action by moving the X-ray tube 2 horizontally or revolving the X-ray tube 2 about the body axis of patient M, and controls setting of a coverage of a collimator (not shown) disposed adjacent the X-ray tube 2. In time of scanning action, the X-ray tube 2 and FPD 3 are moved while maintaining a mutually opposed relationship, so that the FPD 3 may detect X rays emitted from the X-ray tube 2.

The controller 10 has a central processing unit (CPU) and other elements. The memory 11 has storage media, typically a ROM (Read-Only Memory) and RAM (Random Access Memory. The input, unit 12 has a pointing device, typically a mouse, keyboard, joy stick, trackball and/or touch panel. The fluoroscopic apparatus creates images of the patient M, with the FPD 3 detecting X rays transmitted through the patient M, and the image processor 9 performing an image processing based on the X rays detected.

The image processor 9 includes a non-irradiation signal acquiring unit 9a for acquiring a plurality of X-ray detection signals in time of non-irradiation before X-ray irradiation in an imaging event, a lag image acquiring unit 9b for acquiring a lag image based on offset images and gain correcting images described hereinafter, an irradiation signal acquiring unit 9c for acquiring X-ray detection signals in time of X-ray irradiation in an imaging event, and an X-ray image acquiring unit 9d for acquiring an X-ray image serving an intended purpose based on the X-ray detection signals acquired by the irradiation signal acquiring unit 9c and the offset images and gain correcting images described hereinafter, and a lag correcting unit 9e for removing lags from the X-ray image acquired by the X-ray image acquiring unit 9d by using the lag image acquired by the lag image acquiring unit 9b. The lag correcting unit 9e removes lags from the X-ray image by using the lag image to remove any lag-behind parts from the X-ray detection signals, thereby performing a lag correction of the lag-behind parts. The non-irradiation signal acquiring unit 9a corresponds to the non-irradiation signal acquiring device in this invention. The lag image acquiring unit 9b corresponds to the lag image acquiring device in this invention. The irradiation signal acquiring unit 9c corresponds to the irradiation signal acquiring device in this invention. The X-ray image acquiring unit 9d corresponds to the radiation image acquiring device in this invention. The lag correcting unit 9e corresponds to the lag correcting device in this invention.

Figure 9:
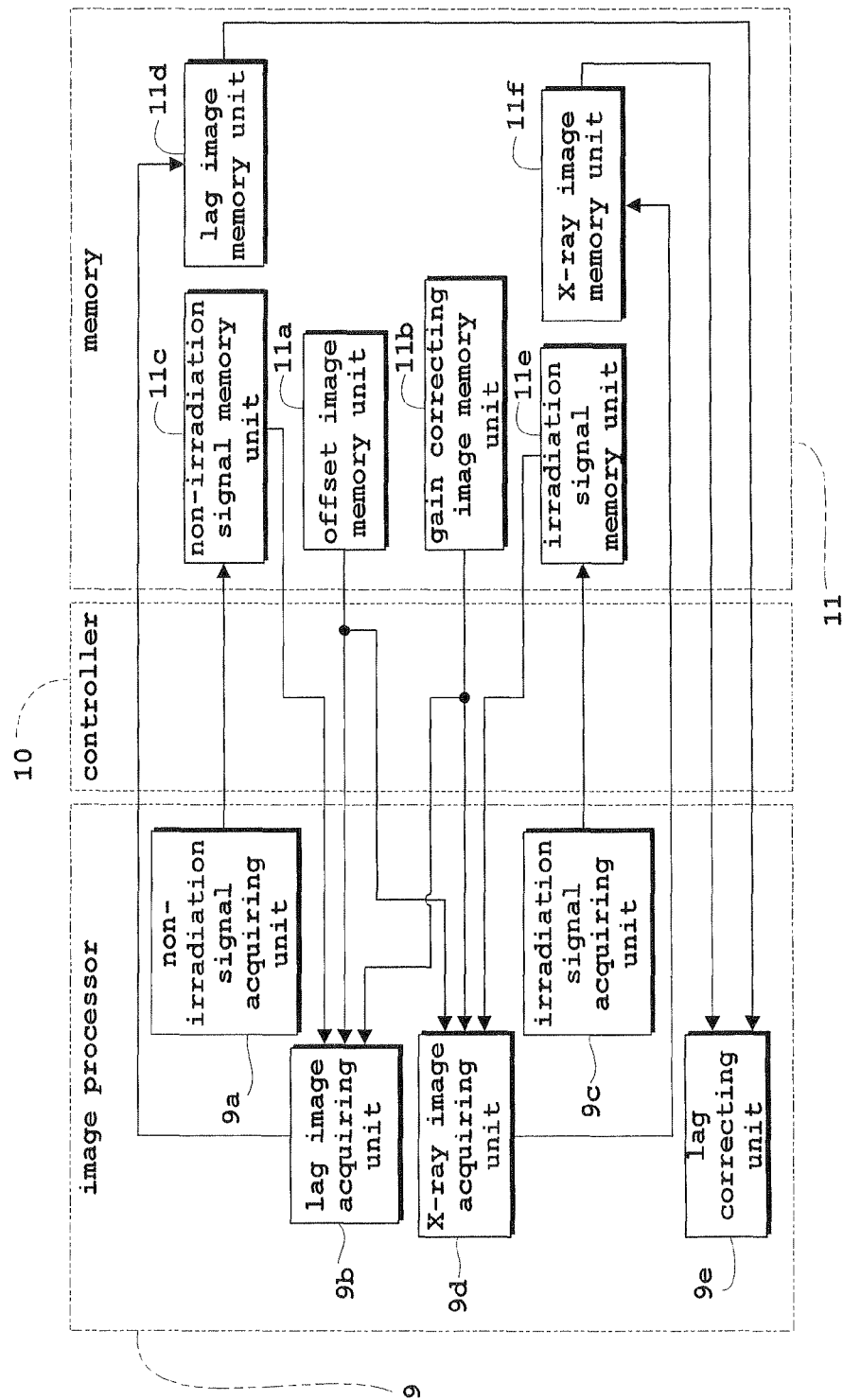
[FIG. 9]Schematic view showing flows of data to and from an image processor and a memory in the first and second embodiments.

The memory 11 includes an offset image memory unit 11a for storing offset images corresponding to a plurality of storage times for accumulating signal information, a gain correcting image memory unit 11b for storing gain correcting images likewise corresponding to a plurality of storage times, a non-irradiation signal memory unit lie for storing X-ray detection signals acquired by the non-irradiation signal acquiring unit 9a in time of non-irradiation, a lag image memory unit 11d for storing the lag image acquired by the lag image acquiring unit 9b, an irradiation signal memory unit lie for storing X-ray detection signals acquired by the irradiation signal acquiring unit 9c in time of irradiation, and an X-ray image memory unit 11f for storing X-ray images acquired by the X-ray image acquiring unit 9d. In Embodiment 1, and also in Embodiment 2 described hereinafter, the lag image acquiring unit 9b acquires a lag image based on the X-ray detection signals of non-irradiation times read from the non-irradiation signal memory unit 11c (see FIG. 9). In Embodiment 3 to follow, a lag image is obtained by a recursive weighted average (recursive process) as described hereinafter (see FIG. 11). The offset image memory unit 11a corresponds to the offset image storage device in this invention. The gain correcting image memory unit 11b corresponds to the gain correcting image storage device in this invention.

As shown in FIG. 2, the FPD 3 includes a glass substrate 31, and thin film transistors TFT formed on the glass substrate 31. As shown in FIGS. 2 and 3, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 2, an X-ray sensitive semiconductor 34 is laminated on the carrier collecting electrodes 33. As shown in FIGS. 2 and 3, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 3, a plurality of data bus lines 39 are connected through amplifiers 38 to a multiplexer 37 for collecting charge signals and outputting as one. As shown in FIGS. 2 and 3, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 38. The carrier collecting electrodes 33 output charge signals (carriers) converted from X rays incident on the detection surface through the X-ray sensitive semiconductor 34, to the data bus lines 39 through, the sources S and drains D of the switching elements 32. The charge signals are provisionally stored in capacitors (not shown) until the switching elements are turned on. The amplifiers 38 amplify the charge signals read, out to the data bus lines 39, and the multiplexer 37 collects the charge signals, and outputs them as one charge signal. The analog-to-digital converter 8 digitizes the outputted charge signal, and outputs it as an X-ray detection signal.

Next, offset correction and gain correction will be described with reference to the explanatory views in FIGS. 4 and 5. FIGS. 4 and 5 illustrate, by way of example, four pixels arranged in two rows and two columns. The offset, images noted above are used to perform offset correction, for removing offset values superimposed on signals. The gain correcting images noted above are used to perform gain correction for equalizing signal levels of pixels to be outputted.

Offset components (i.e. offset values) are superimposed, on signal levels of the pixels (i.e. pixel values) based on the X-ray detection signals when, outputted from the image processor 9. Specifically, as shown in FIG. 4 (*a*), offset values O (={$O_{11}, O_{12}, O_{21}, O_{22}$}) due to dark current are outputted in time of non-irradiation. As shown in FIG. 4 (*b*), the offset values O in time of non-irradiation are superimposed on pixel values S (={$S_{11}, S_{12}, S_{21}, S_{22}$}) to output values (S+O) (={$S_{11}+O_{11}, S_{12}+O_{12}, S_{21}+O_{21}, S_{22}+O_{22}$}). Thus, offset values O in time of non-irradiation, i.e., offset images, are determined and stored in the offset image memory unit 11*a* in advance of an imaging event.

On the other hand, while the signal levels of the pixels (i.e. pixel values) based on the X-ray detection signals are outputted according to the value of the amplification factor (gain) of the amplifier 38 of FPD 3 (see FIG. 3), pixel values S outputted are variable from pixel to pixel due to individual specificities such as of the switching elements 32 corresponding to the respective pixels. Specifically, assume that, as shown in FIG. 5 (*a*), varied pixel values S {$S_{11}, S_{12}, S_{21}, S_{22}$} are outputted when the same dose of X rays is incident on each pixel. It is further assumed that, by adjusting each gain, as shown in FIG. 5 (*b*), pixel values S outputted are equalized to be {$S_O, S_O, S_O, S_O$}. Thus, gain correcting images G are determined as {$S_{11}/S_O, S_{12}/S_O, S_{21}/S_O, S_{22}/S_O$} and stored in the gain correcting image memory unit 11*b* in advance of an imaging event.

Figure 6:
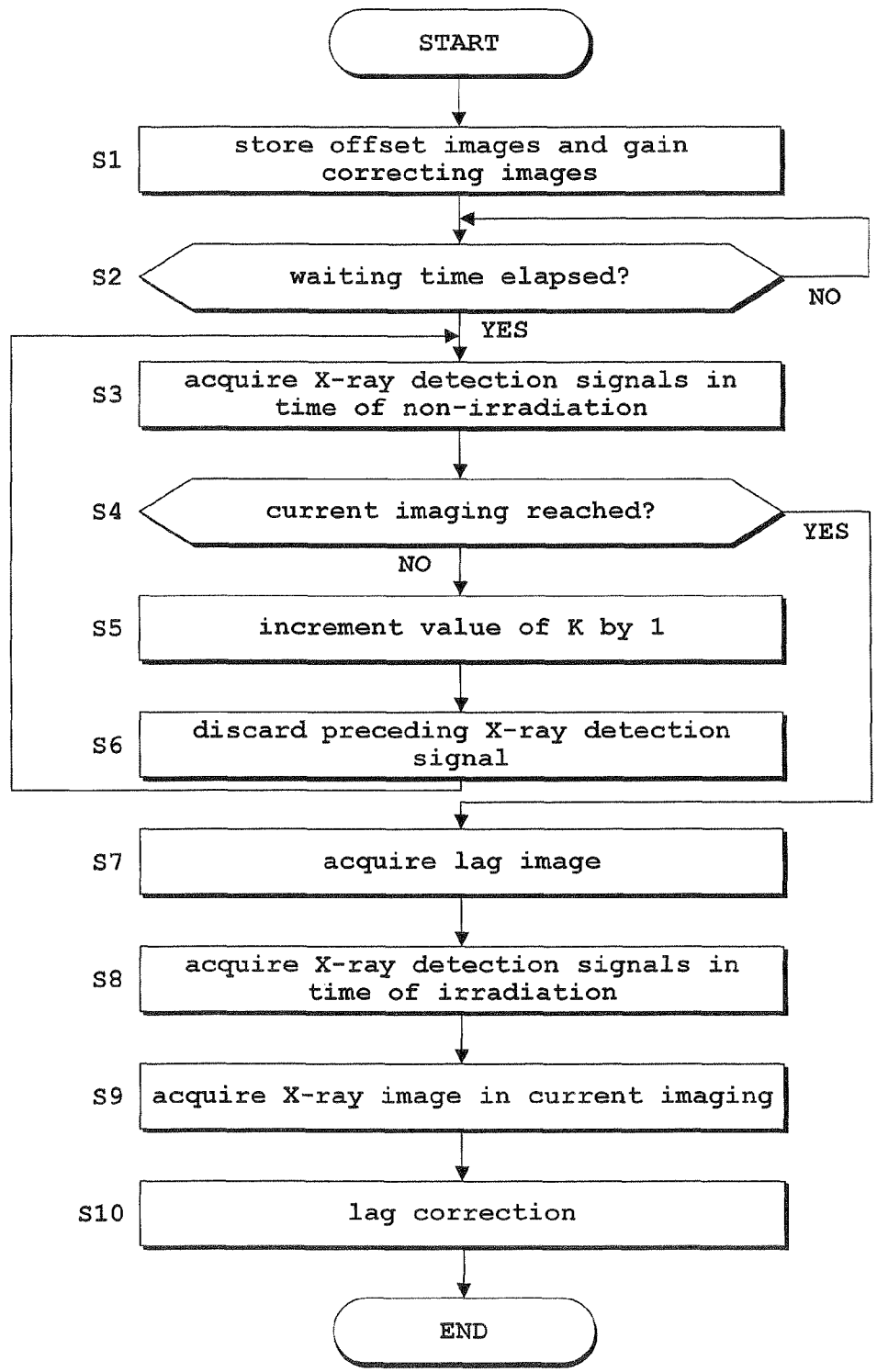
[FIG. 6]Flow chart showing a series of signal processing by a non-irradiation signal acquiring unit, a lag image acquiring unit, an irradiation signal acquiring unit, an X-ray image acquiring unit and a lag correcting unit in a first embodiment.

Next, a series of signal processing by the non-irradiation signal acquiring unit 9*a*, lag image acquiring unit 9*b*, irradiation signal acquiring unit 9*c*, X-ray image acquiring unit 9*d* and lag correcting unit 9*e* in Embodiment 1 will be described with reference to the flow chart shown in FIG. 6 and the time chart shown in FIG. 7. This processing will be described by taking for example what takes place from an end of X-ray irradiation in a preceding imaging event to X-ray irradiation in a current imaging event, and in preparation, for offset images and gain correcting images before the imaging events.

(Step S1) Store Offset Images and Gain Correcting Images

The offset images and gain correcting images have different properties according to storage times for accumulating signal information (electric charges) corresponding to X-ray detection, signals. Thus, as shown in FIG. 8, these images are stored as corresponding to the respective storage times in advance of the imaging events.

In Embodiment 1, and also in Embodiments 2 and 3 described, hereinafter, storage times in time of non-irradiation are regarded as sampling time intervals (e.g. 1/30 second), represented by cycle ΔT1, for sampling signals in time of non-irradiation. On the other hand, as noted also in the section herein "PROBLEMS TO BE SOLVED BY THE INVENTION", in practice, the storage time immediately after an image pick-up is dependent on a pulse width of X rays variable in time with the thickness and the like of patient M. In Embodiment 1, and also in Embodiments 2 and 3 described hereinafter. X-ray irradiation time (pulse width of X rays) for image pickup is synchronized with cycle ΔT1, and is set to two or more times the cycle ΔT1. In this example, irradiation times (pulse widths of X rays) enabling image pickup are regarded as three different times, which are ΔT1, ΔT2=ΔT1×2, and ΔT3=ΔT1×3.

An offset image and a gain correcting image are acquired for each of these storage times (sampling times and irradiation times). The offset images are stored in the offset image memory unit 11*a*, and the gain correcting images in the gain correcting image memory unit 11*b*.

Figures 7, 8:
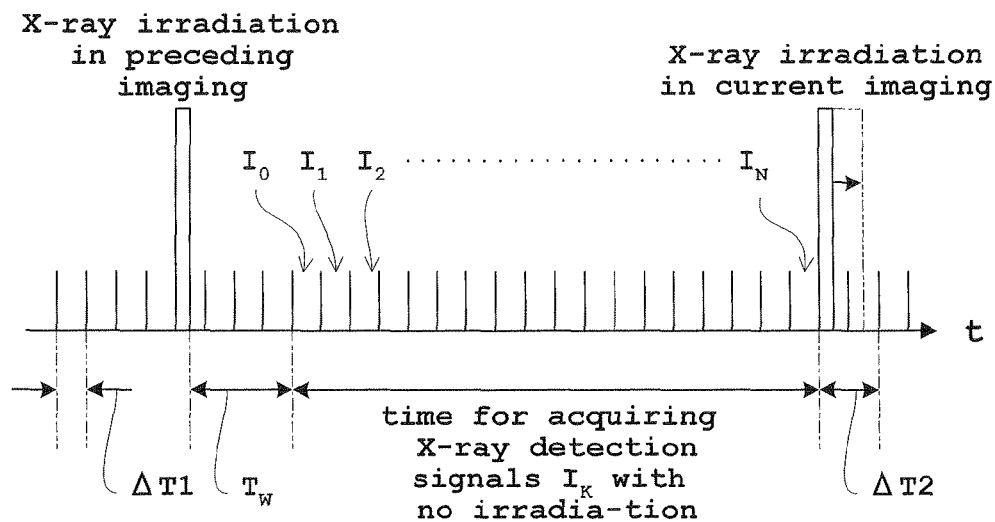
[FIG. 7]Time chart showing X-ray emissions and acquisition of X-ray detection signals.
[FIG. 8]Schematic view showing storage of offset images gain correcting images corresponding to storage times.

In FIG. 8, ΔT1 corresponds to offset image O1 and gain correcting image G1 obtained in time of ΔT1, ΔT2 corresponds to offset image O2 and gain correcting image G2 obtained in time of ΔT2, and ΔT3 corresponds to offset image O3 and gain correcting image G3 obtained in time of ΔT3. This step S1 corresponds to the offset image storing step and gain correcting image storing step.

(Step S2) Waiting Time Elapsed?

A checking is made whether or not a predetermined waiting time $T_W$ has elapsed from the end of X-ray irradiation in the preceding imaging event as shown in FIG. 7. Immediately after the end of irradiation, a lag-behind part includes numerous short time constant components or medium time constant components. These short or medium time constant components attenuate in a short time. After their attenuation, long time constant components become dominant, and remain with substantially the same intensity. The waiting time $T_W$ is provided so that X-ray detection signals may be acquired in time of non-irradiation after lapse of the predetermined time from X-ray irradiation in the preceding imaging event. Upon lapse of the waiting time $T_W$, the operation proceeds to next step S3. Whether the waiting time $T_W$ has passed or not may be determined by means of a timer (not shown). That is, the timer is reset to "0" to start counting simultaneously with the termination of X-ray irradiation in the preceding imaging event. It may be determined, when a count corresponding to the waiting time $T_W$ is reached, that the waiting time $T_W$ has passed.

The waiting time $T_W$, preferably, is about 15 seconds although this depends on the lag characteristics of individual FPD 3, and the waiting time $T_W$ of about 30 seconds should be sufficient. The longer waiting time $T_W$, e.g. at least 30 seconds, is the better. However, an excessively long time means an extended interval between imaging events, it is realistic for practical purposes to set the waiting time $T_W$ to about 3 seconds.

(Step S3) Acquire X-Ray Detection Signals in Time of Non-Irradiation

The non-irradiation signal acquiring unit 9*a* successively acquires X-ray detection signals at sampling time intervals ΔT1 in time of non-irradiation after lapse of the waiting time $T_W$. The number of sampling times before start of the X-ray irradiation in the current imaging operation is set to (N+1) (note that K=0, 1, 2, . . . , N−1 and N), with K=0 indicating the first signal acquired immediately after lapse of the waiting time $T_W$. With a (K+1)th X-ray detection, signal regarded as $I_K$, the first X-ray detection signal acquired immediately after lapse of the waiting time $T_W$ is $I_0$, and the X-ray detection signal acquired immediately before start of X-ray irradiation in the current imaging event is $I_N$. It is assumed here that steps S3-S6 are successively executed for each sampling time interval ΔT1.

(Step S4) Current Imaging Reached?

A checking is made whether or not the time for acquiring X-ray detection signals in step S3, i.e. sampling time, has reached the start of X-ray irradiation in the current imaging event (whether or not K=N+1). When it has been reached, the operation jumps to step S7. Otherwise, next step S5 is executed.

(Step S5) Increment Value of K by 1

The value of subscript K is incremented by 1 for a next sampling.

(Step S6) Discard Preceding X-Ray Detection Signal

X-ray detection signal $I_K$ acquired by the non-irradiation signal acquiring unit 9a in step S3 is written and stored in the non-irradiation signal memory unit 11e. At this time, X-ray detection signal $I_{K-1}$ acquired before X-ray detection signal $I_K$ is discarded as no longer necessary. Thus, only the latest X-ray detection signal remains stored, in the non-irradiation signal memory unit 11c. When, the operation proceeds to step S6 after incrementing K=0 to K=1 in step S5, there exits no X-ray detection signal preceding signal $I_0$, and thus no signal to be discarded. Then, the operation returns to step S3 for a next sampling, and repeats steps S3-S6 for each of the sampling time intervals ΔT1. While, in Embodiment 1, preceding X-ray detection signals are discarded and only the latest X-ray detection signal is retained, it is of course not absolutely necessary to discard the earlier signals. The above steps S3-S6 correspond to the non-irradiation signal acquiring step in this invention.

(Step S7) Acquire Lag Image

When the sampling time has reached the start of X-ray irradiation in the current imaging event in step S4, the (N+1)th X-ray detection signal $I_N$ acquired in step S3 is employed as a lag image. That is, the lag image acquiring unit 9b reads from the non-irradiation signal memory unit 11c the X-ray detection signal $I_N$ acquired immediately before the start of X-ray irradiation in the current imaging event, and acquires the X-ray detection signal $I_N$ as a lag image. Thus, the lag image L=$I_N$. However, for this lag image L, an offset image and a gain correcting image are taken into consideration, and a lag image L' taking the offset image and gain correcting image into consideration is derived from the following equation (1):

$$L'=(L-O1)\div G1 \quad (1)$$

Since the storage time at this time is sampling time ΔT1 in time of non-irradiation, the offset image O1 corresponding to sampling time ΔT1 is read from the offset image memory unit 11a, and the gain correcting image G1 corresponding to sampling time ΔT1 is read from the gain correcting memory unit 11b. The lag image acquiring unit 9b derives a final lag image L' from the above equation (1). The lag image L' acquired by the lag image acquiring unit 9b is written and stored in the lag image memory unit 11d. This step S7 corresponds to the lag image acquiring step in this invention.

Each of the gain correcting images G1-G3, including the gain correcting image G1 used, in the above equation (1) and gain correcting image G2 used in equation (2) described hereinafter, also includes offset components. It is therefore preferable to obtain a gain correcting image G' by subtracting offset image O from gain correcting image G, as G−O=G', and to substitute the gain correcting image G', instead of gain correcting image G, into the equations, such as equation (1) and equation (2).

(Step S8) Acquire X-Ray Detection Signals in Time of Irradiation

Upon completion of X-ray irradiation in the current imaging event, the irradiation signal acquiring unit 9c acquires X-ray detection signals in time of irradiation resulting from this irradiation. The X-ray detection signals in time of irradiation acquired, by the irradiation signal acquiring unit 9c are written and stored in the irradiation signal memory unit 11e. This step S8 corresponds to the irradiation signal acquiring step in this invention.

(Step S9) Acquire X-Ray Image in Current Imaging

The X-ray detection signals in time of irradiation acquired in step S8 are referenced X. For the X-ray detection signals X in time of irradiation, the offset images and gain correcting images are taken into consideration, and an X-ray image X' taking the offset, images and gain correcting images into consideration is derived from the following equation (2).

$$X'=(X-O2)\div G2 \quad (2)$$

The storage time at this time is set to ΔT2 (=ΔT1×2) which is twice the sampling time (i.e. cycle) ΔT1 in time of non-irradiation as shown in FIG. 7 (see the two-dot chain line in FIG. 7). The offset image O2 corresponding to sampling time ΔT2 is read from the offset image memory unit 11a, and the gain correcting image G2 corresponding to sampling time ΔT2 is read from the gain correcting image memory unit 11b. Then, the X-ray image acquiring unit 9d derives X-ray image X' in this imaging event from the above equation (2). The X-ray image X' acquired by the X-ray image acquiring unit 9d is written, and stored in the X-ray image memory unit 11f. This step S9 corresponds to the radiation image acquiring step in this invention. The X-ray image corresponds to the radiographic image serving an intended purpose in this invention.

(Step S10) Lag Correction

The lag correcting unit 9e reads the lag image L' acquired in step S7 from the lag image memory unit 11d, reads the X-ray image X' acquired in step S9 from the X-ray image memory unit 11f, and subtracts the lag image L' from the X-ray image X'. An X-ray image Y after the lag correction is expressed by Y=X'−L'.

In actual situations, the timing of X-ray irradiation in the current imaging event is not necessarily determined beforehand. Therefore, the time of reaching K=N+1 is not necessarily known in advance. Then, in actual situations, steps S3-S6 described above are repeated for each sampling time interval, and the sampling time reaching the start of X-ray irradiation in the current imaging event in step S4 is regarded as the time of reaching K=N+1. Where the timing of X-ray irradiation in the current imaging event is determined in advance, the time of reaching K=N+1 is also known in advance, of course. In such a case, a value of N may be set in advance so that the sampling time may reach the start of X-ray irradiation in the current imaging event in accordance with the timing of reaching K=N+1. This step S10 corresponds to the lag correcting step in this invention.

The technique of removing a lag from X-ray image X' by using lag image L' is not limited to the technique of subtracting lag image L' directly from X-ray image X'. In Embodiment 1, for example, the storage time of the lag image is sampling time ΔT1 in time of non-irradiation, and the storage time of the X-ray image is ΔT2 (=ΔT1×2) which is twice the sampling time ΔT1. The two images are different in mode regarding storage time. In such a case, it is preferable to subtract, twice the lag image (however, the gain [amplification factor] of amplifier 38 remains unchanged). In this case, the equation becomes Y=X'−2×L'.

According to Embodiment 1 having the described construction, offset images are used to carry out offset correction for removing offset values superimposed on signals. The offset images corresponding to a plurality of storage times for accumulating signal information are stored, in the offset, image memory unit 11a. Gain correcting images are used to carry out gain correction for equalizing signal levels of pixels to be outputted. The gain, correcting images corresponding to the plurality of storage times for accumulating signal information are stored in the gain correcting image memory unit 11b.

The non-irradiation signal acquiring unit 9a acquires a plurality of X-ray detection signals ($I_0, I_1, I_2, ---, I_{N...1}, I_N$ in Embodiment 1) detected from the flat panel X-ray detector (FPD) 3 in time of non-irradiation before irradiation of X rays in an imaging event. Based on these X-ray detection signals acquired by the non-Irradiation signal acquiring unit 9a, the offset, image (O1 in the above equation (1) in Embodiment 1) stored in the above offset image memory unit 11a and corresponding to the storage time ($\Delta T1$ in Embodiment 1) for the non-irradiation signal acquiring unit 9a, and the gain correcting image (G1 in the above equation (1) in Embodiment 1) stored in the above gain correcting image memory unit 11b and corresponding to the storage time for the non-irradiation signal acquiring unit 9a, the lag image acquiring unit 9b acquires a lag image from the above equation (1).

On the other hand, the irradiation signal acquiring unit 9c acquires X-ray detection signals detected from the FPD 3 in time of X-ray irradiation in an imaging event. Based on the X-ray detection signals acquired by the irradiation signal acquiring unit 9c, the offset image (O2 in the above equation (2) in Embodiment 1) stored in the above offset, memory unit 11a and corresponding to the storage time for the irradiation signal acquiring unit 9c, and the gain correcting image (O2 in the above equation (2) in Embodiment 1) stored in the above gain correcting image memory unit 11b and corresponding to the storage time ($\Delta T2$ in Embodiment 1) for the irradiation signal acquiring unit 9c, the X-ray image acquiring unit 9d acquires an X-ray image serving an intended purpose from the above equation (2).

Then, the lag correcting unit 9e carries out a lag correction of lag-behind parts by removing lags, using the lag image acquired by the lag image acquiring unit 9b, from the X-ray image acquired by the X-ray image acquiring unit 9d, thereby removing from the X-ray detection signals the lag-behind parts included in the X-ray detection signals.

Thus, there is no need, to carry out lag correction by performing recursive computations the number of times X-ray detection signals are sampled, as described in Patent Document 2 noted hereinbefore. Further, the lag image forming the basis for the above lag correction, and the X-ray image which, is the target, of the lag correction, take into consideration the offset images and lag correcting images corresponding to the respective storage times ($\Delta T1$ and $\Delta T2$ in Embodiment 1). It becomes possible to perform appropriately also offset correcting and lag correcting images according to the storage times by lag correction. A lag-behind part may therefore be eliminated from an X-ray detection signal in a simple way. Further, there is no need to use backlight as used in Patent Document 1 noted hereinbefore. This avoids complication of the apparatus construction.

In Embodiment 1, and also in Embodiments 2 and 3 to follow, a plurality of X-ray detection signals are acquired in time of non-irradiation after lapse of the predetermined time (i.e. the waiting time $T_W$ in Embodiment 1) from X-ray irradiation in a preceding imaging event. Consequently, a plurality of X-ray detection signals are acquired in time of non-irradiation before X-ray irradiation in a current imaging event. When the X-ray irradiation in the preceding imaging event is completed and a transition is made to a state of non-irradiation, short time constant components or medium time constant components of a lag-behind part attenuate in a short time. After their attenuation, long time constant components become dominant, and remain with substantially the same intensity. Consequently, when an X-ray detection signal is acquired immediately after completion of the X-ray irradiation in the preceding imaging event, short and medium time constant components are included in the signals acquired. The lag-behind part having the short and medium time constant components cannot be eliminated from the signal accurately. Thus, in Embodiment 1, a plurality of X-ray detection signals are acquired in time of non-irradiation after lapse of the predetermined time from the X-ray irradiation in the preceding imaging event. Consequently a plurality of X-ray detection signals are acquired in time of non-irradiation before X-ray irradiation in the current imaging event. The signals may be acquired in a state of including only the long time constant components which remain after lapse of the predetermined time. The signals are free from the short and medium time constant components, and a lag-behind part having the long time constant components may be eliminated accurately.

Embodiment 2

Next, Embodiment 2 of this invention will be described with reference to the drawings. Like reference signs will be used to identify like parts which are the same as in Embodiment 1 and will not be described again. A fluoroscopic apparatus in Embodiment 2 is similar to the apparatus in Embodiment 1, and only the series of signal processing by the non-irradiation signal acquiring unit 9a, lag image acquiring unit 9b, X-ray image acquiring unit 9d and lag correcting unit 9e is different from that in Embodiment 1.

Figure 10:
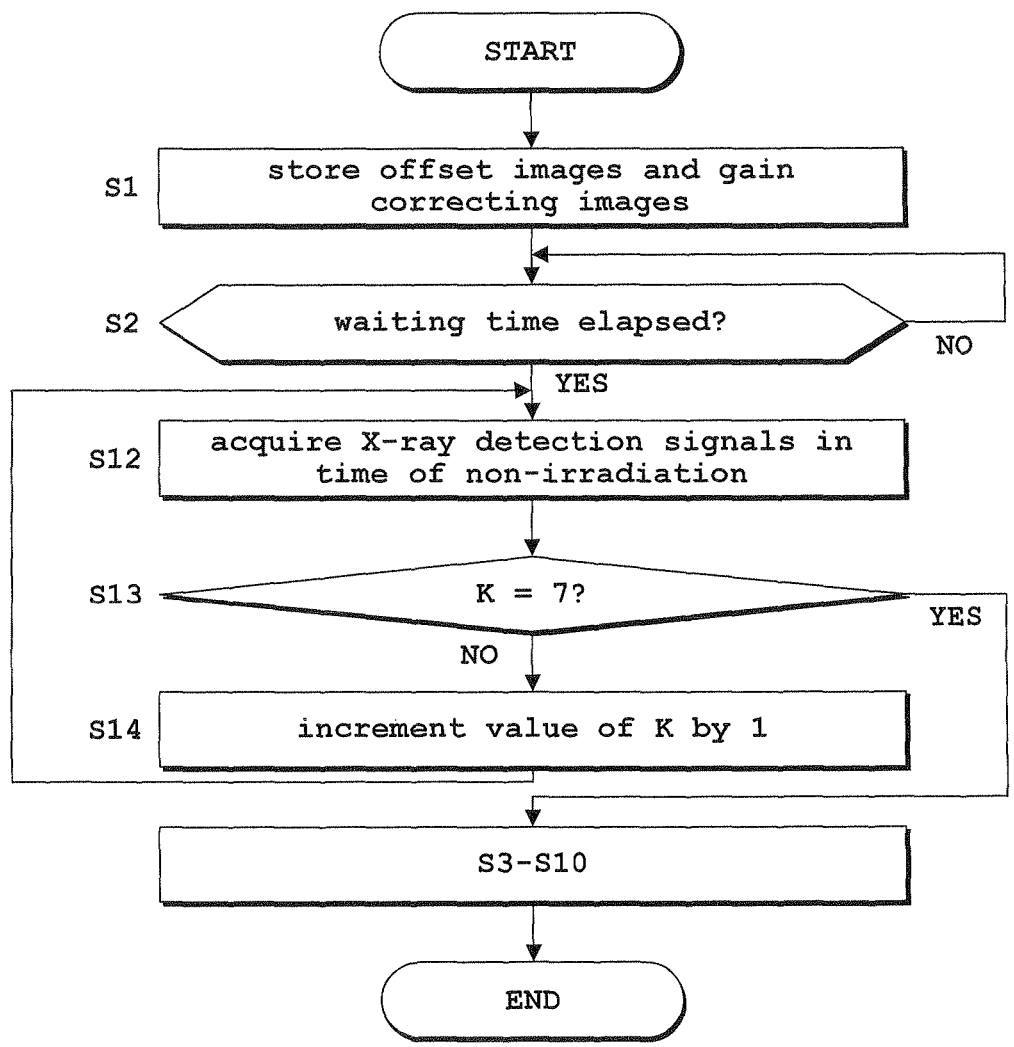
[FIG. 10]Flow chart showing a series of signal processing by a non-irradiation signal acquiring unit, a lag image acquiring unit, an irradiation signal acquiring unit, an X-ray image acquiring unit and a lag correcting unit in the second embodiment.

The series of signal processing by the non-irradiation signal acquiring unit 9a, lag image acquiring unit 9b, X-ray image acquiring unit 9d and lag correcting unit 9e in Embodiment 2 will be described with reference to the flow chart of FIG. 10. Like numerals are affixed to like steps in Embodiment 1 and will not be described again.

(Step S1) Store Offset Images and Gain Correcting Images

As in Embodiment 1 described hereinbefore, offset images and gain correcting images corresponding to storage times (sampling times and irradiation times) are obtained for each storage time. These images are stored in the offset image memory unit 11a or gain correcting image memory unit 11b.

(Step S2) Waiting Time Elapsed?

As in Embodiment 1 described hereinbefore, a checking is made whether or not the waiting time $T_W$ has elapsed from the end of X-ray irradiation in the preceding imaging event. Upon lapse of the waiting time $T_W$, the operation proceeds to next step S12.

(Step S12) Acquire X-Ray Detection Signals in Time of Non-Irradiation

As in Embodiment 1 described hereinbefore. X-ray detection signals are successively acquired at sampling time intervals $\Delta T1$ (e.g. 1/30 second) in time of non-irradiation after lapse of the waiting time $T_W$. In Embodiment 2, as will become clear from the following description, the signals from the first X-ray detection signal $I_0$ acquired immediately after the waiting time $T_W$ to the seventh X-ray detection signal $I_6$ remain stored in the non-irradiation signal memory unit 11c, instead of being discarded, until acquisition of the eighth X-ray detection signal $I_7$ (i.e. K=7). It is to be noted that steps S12-S14 are repeated at each of the sampling time intervals.

(Step S13) K=7?

A checking is made whether or not subscript K has reached 7, that is whether the sampling time has reached to the eighth (i.e. K=7). When K=7, the operation jumps to step S3. Otherwise, next step S14 is executed.

(Step S14) Increment Value of K by 1

As in Embodiment 1 described hereinbefore, the value of subscript K is incremented by 1 for a next sampling. X-ray detection signals $I_K$ acquired by the non-irradiation signal acquiring unit 9a in step S12 are successively written and stored in the non-irradiation signal memory unit 11c until acquisition of the eighth X-ray detection signal $I_7$ (i.e. K=7). At this time, X-ray detection signal $I_{K-1}$ acquired before X-ray detection signal $I_K$ is not discarded but is retained in the non-irradiation signal memory unit 11c until eight X-ray detection signals accumulate in the non-irradiation signal memory unit 11a. Then, the operation returns to step S12 for a next sampling, and repeats steps S12-S14 for each of the sampling time intervals.

(Step S3)-(Step S10)

When the sampling time has reached the start of X-ray irradiation for the current imaging event in step S13, steps S3-S10 similar to Embodiment 1 are executed. However, eight X-ray detection signals are constantly stored in the non-irradiation signal memory unit 11e, and when the latest X-ray detection signal is newly stored in the non-irradiation signal memory unit 11c in step S6, the oldest X-ray detection signal only is discarded. When the sampling time has reached the start of X-ray irradiation in the current imaging event in step S4, a lag image L is created based on the eight signals from (N−6)th X-ray detection signal $I_{N-7}$ to (N+1)th X-ray detection signal $I_N$ acquired in step S3. Further, a lag image L' taking the offset image and gain correcting image into consideration is derived from equation (1) above. Specifically, a lag image is derived from an average of these signals ($L=\Sigma I_i/8$, where $\Sigma$ is a total of i=N−7 to N). The process from acquisition of the lag image L to the lag correction is the same as in Embodiment 1, and its description is omitted.

According to Embodiment 2 having the described construction, as in Embodiment 1, offset images and gain correcting images corresponding to a plurality of storage times ($\Delta T1$, $\Delta T2$ and $\Delta T3$) are stored before an imaging event, and a lag image and an X-ray image are acquired based on these stored images. Then, lag correction is carried out to remove lags from the X-ray image using the lag image. In this way, from the X-ray image taking info consideration the offset images and gain correcting images corresponding to the storage times, lags are removed using the lag image which similarly takes into consideration the offset images and gain correcting images corresponding to the storage times. Lag-behind parts, including offset and gain components, are removed from X-ray detection signals in a simple way.

In Embodiment 1, random noise components of X-ray image Y after the lag correction become $2^{1/2}$ times those of image X, thereby lowering the signal-to-noise ratio by 41% ($=(2^{1/2}-1)$). In order to suppress this deterioration, Embodiment 2, as distinct from Embodiment 1, derives the lag image L by directly using the plurality of X-ray detection signals ($I_{N-7}, I_{N-6}, \ldots, I_{N-1}$ and $I_N$ in Embodiment 2). In this case, the random noise components of X-ray image Y after the lag correction cause deterioration no more than 6% of the X-ray image X before the correction. Thus, the lag correction can be effected without lowering the signal-to-noise ratio.

In Embodiment 2, the lag image L is obtained by directly using eight. X-ray detection signals. However, the invention is not limited to a particular number of X-ray detection, signals to be used. Further, although the lag image L is derived from an average of the signals, the lag image L may be derived from a median. A histogram showing intensities of the signals may be formed, to derive a mode as lag image L from the histogram. Thus, the invention is not limited to a particular way of deriving the lag image L.

Embodiment 3

Figure 11:
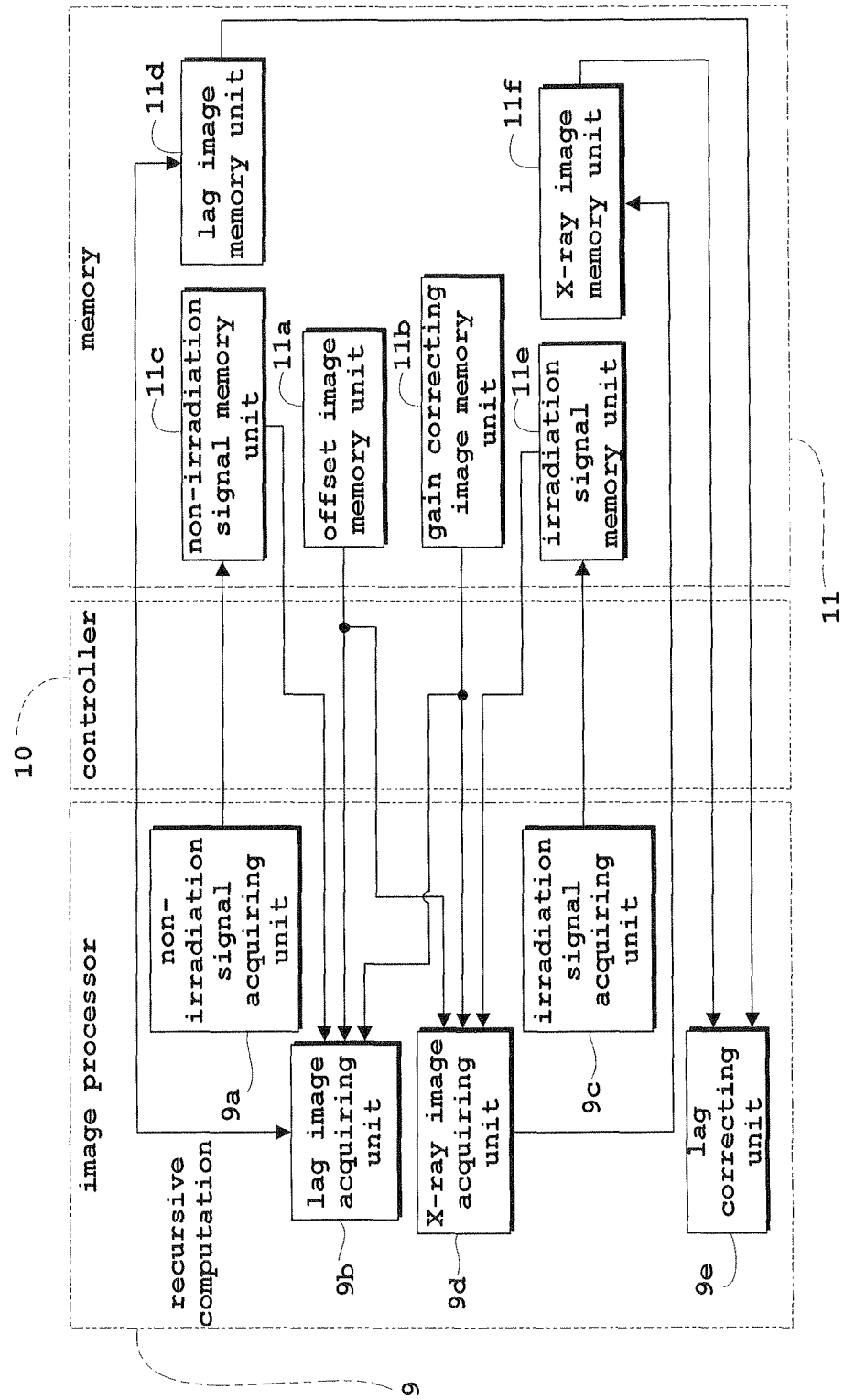
[FIG. 11]Schematic view showing flows of data to and from an image processor and a memory in a third embodiment.

Next, Embodiment 3 of this invention will be described with reference to the drawings. FIG. 11 is a schematic view showing flows of data to and from an image processor and a memory in Embodiment 3. Like reference signs will be used to identify like parts which are the same as in Embodiments 1 and 2, and will not be described again. A fluoroscopic apparatus in Embodiment 3 is the same as the apparatus in Embodiments 1 and 2, except the flows of data to and from the image processor 9 and memory 11 shown in FIG. 11. The series of signal processing by the non-irradiation signal acquiring unit 9a, lag image acquiring unit 9b, irradiation signal acquiring unit 9c, X-ray image acquiring unit 9d and lag correcting unit 9e also is different from those in Embodiments 1 and 2.

In Embodiment 3, as shown in FIG. 11, the lag image acquiring unit 9b acquires a lag image L (before taking the offset images and gain correcting images into consideration) by recursive computation based on the X-ray detection signals in time of non-irradiation read from the non-irradiation signal memory unit 11c and a preceding lag image read from the lag image memory unit 11d. The acquisition of a lag image L by recursive computation will be described with reference to the flow chart of FIG. 12. The lag image acquiring unit 9b acquires a lag image L' using equation (1) above, based on the offset images and gain correcting images, through recursive computation. The lag correcting unit 9e removes the lag image read from the lag image memory unit 11d from an X-ray image obtained in the current imaging event, in the same way as in Embodiments 1 and 2 described hereinbefore.

Figure 12:
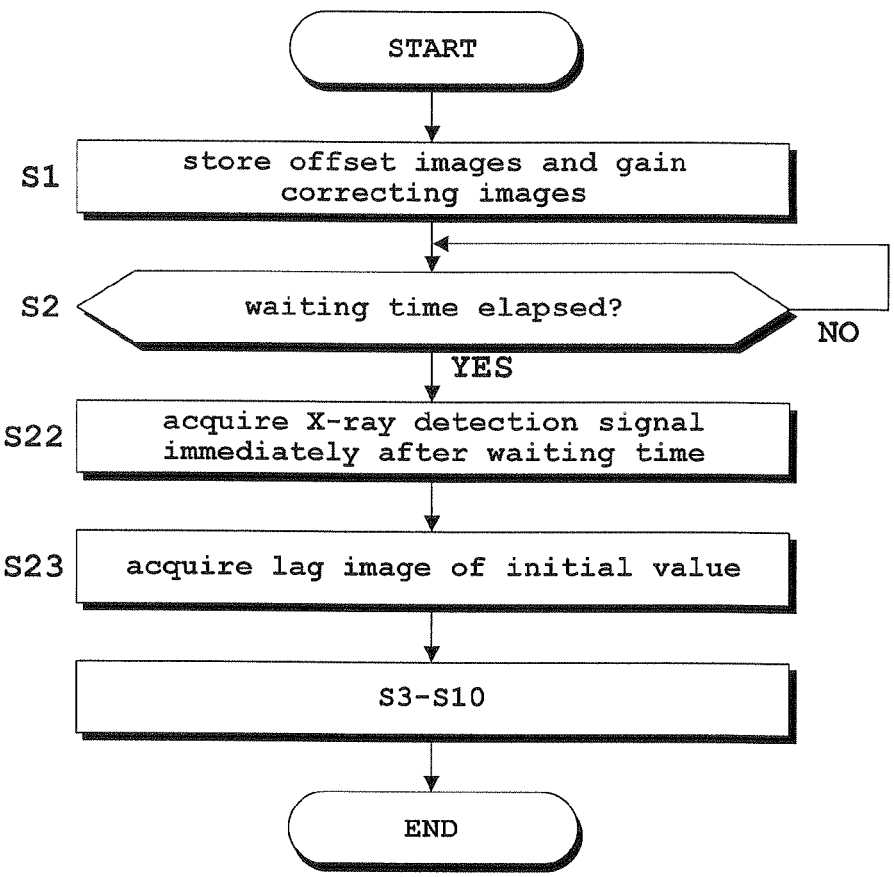
[FIG. 12]Flow chart showing a series of signal processing by a non-irradiation signal acquiring unit, a lag image acquiring unit, an irradiation signal acquiring unit, an X-ray image acquiring unit and a lag correcting unit in the third embodiment.

Next, the series of signal processing by the non-irradiation signal acquiring unit 9a, lag image acquiring unit 9b, irradiation signal acquiring unit 9c, X-ray image acquiring unit 9d and lag correcting unit 9e in Embodiment 3 will be described with reference to the flow chart of FIG. 12. Like numerals are affixed to like steps in Embodiments 1 and 2 and will not be described again.

(Step S1) Store Offset Images and Gain Correcting Images

As in Embodiments 1 and 2 described hereinbefore, offset images and gain correcting images corresponding to storage times (sampling times and irradiation times) are obtained for each storage time. These images are stored in the offset image memory unit 11a or gain correcting image memory unit 11b.

(Step S2) Waiting Time Elapsed?

As in Embodiments 1 and 2 described hereinbefore, a checking is made whether or not the waiting time $T_W$ has elapsed from the end of X-ray irradiation in the preceding imaging event. Upon, lapse of the waiting time $T_W$, the operation proceeds to next, step S22.

(Step S22) Acquire X-Ray Detection Signal Immediately after Waiting Time

As in Embodiments 1 and 2 described hereinbefore. X-ray detection signals are successively acquired at sampling time intervals $\Delta T1$ (e.g. 1/30 second) in time of non-irradiation after lapse of the waiting time $T_W$. The first X-ray detection signal $I_0$ is acquired immediately after the waiting time $T_W$, which is written and stored in the non-irradiation signal memory unit 11c.

(Step S23) Acquire Lag Image of Initial Value

The lag image acquiring unit 9b reads this X-ray detection signal $I_0$ from the non-irradiation signal memory unit 11c, and acquires from the X-ray detection signal $I_0$ a lag image $L_0$ as an initial value of lag image L (before taking the offset images and gain correcting images into consideration). The lag image $L_0$ of initial value acquired by the lag image acquiring unit 9b is written and stored in the lag image memory unit 11d.

(Step S3)-(Step S10)

After the lag image $L_0$ of initial value is acquired in step S23, steps S3-S10 similar to Embodiment 1 are executed. However, the X-ray detection signals acquired in time of non-irradiation in step S3 are the second X-ray detection signal $I_1$ et seq. When acquiring the lag image L (before taking the offset images and gain correcting images into consideration) in step S7, an (N+1)th lag image $L_N$ is derived by recursive computation from the X-ray detection signals $I_N$ in time of non-irradiation read from the non-irradiation signal memory unit 11c and the preceding lag image $L_{N...1}$ read from the lag image memory unit 11d. In Embodiment 3, the lag image $L_N$ is derived by a recursive weighted average (hereinafter referred to as "recursive process" as appropriate) from the following equation (3):

$$L_N = (1-P) \times L_{N...1} + P \times I_N \quad (3)$$

In this process, $I_0 = L_0$ as noted above. P is a load ratio which takes a value of 0 to 1.

When the latest lag image $L_N$ is acquired as lag image L in step S7, only the lag image $L_{N...1}$ preceding the lag image $L_N$, i.e. only the lag image $L_{N...1}$ serving as the basis of the recursive process expressed by equation (3) above, is required. The remaining lag images L, i.e. lag image $L_{N...2}$ before last and lag images $L_{N...3}, \ldots, L_1$ and $L_0$ acquired earlier are unnecessary. Thus, once the latest lag image $L_N$ is stored in the lag image memory unit 11d, only the immediately preceding lag image $L_{N...1}$ is retained and the other lag images L are discarded. It is of course not absolutely necessary to discard the lag image $L_{N...2}$ before last and earlier lag image $L_{N...3}$ and so on.

Further, the latest lag image $L_N$ obtained through the series of recursive processes is regarded as L, and based on the offset images and gain correcting images, the lag image acquiring unit 9b acquires, using equation (1) above, lag image L' taking the offset images and gain correcting images into consideration.

According to Embodiment 3 having the described construction, as in Embodiments 1 and 2, from the X-ray image taking into consideration the offset images and gain correcting images corresponding to the storage times, lags are removed using the lag image which similarly takes into consideration the offset images and gain correcting images corresponding to the storage times. Lag-behind parts, including offset and gain components, are removed from X-ray detection signals in a simple way.

In Embodiment 3, a plurality of X-ray detection signals are successively acquired at sampling time intervals $\Delta T1$ (e.g. 1/30 second) in time of non-irradiation. Assuming a certain point in time of non-irradiation to be the (N+1)th, a lag image L is obtained based on a plurality of X-ray detection signals including the (N+1)th signal so far acquired successively. That is, an (N+1)th lag image $L_N$ is obtained. For this purpose, the recursive computation is repeated based on the X-ray detection signal $I_N$ acquired at the (N+1)th point of time, and a lag image L (before taking the offset images and gain correcting images into consideration) based on a plurality of X-ray detection signals successively acquired up to the Nth point, of time before the (N+1)th point of time, that is the lag image $L_{N...1}$ before the lag image $L_N$.

Whenever an X-ray detection signal is successively acquired in time of non-irradiation, the recursive computation is repeated based on the latest X-ray detection signal $I_N$ acquired, and the lag image (i.e. preceding lag image) $L_{N...1}$ resulting from a plurality of X-ray detection signals successively acquired in the past. The lag image $L_N$ ultimately obtained is a lag image L before taking the offset images and gain correcting images into consideration. Further, the lag image L' derived from equation (1) above and taking the offset images and gain correcting images into consideration is a goal image used as the basis for the lag correction. Only the newest lag image $L_N$ obtained by recursive computation and the lag image (i.e. the lag image used as the basis of the recursive computation) $L_{N...1}$ before the lag image may be retained, with the other lag images (i.e. the lag images earlier than the above two lag images) discarded. Then, for example, the lag image memory unit 11d may have a storage region just for two frames, i.e. enough for storing two images. This provides an advantage of simplifying the construction.

Figure 13:
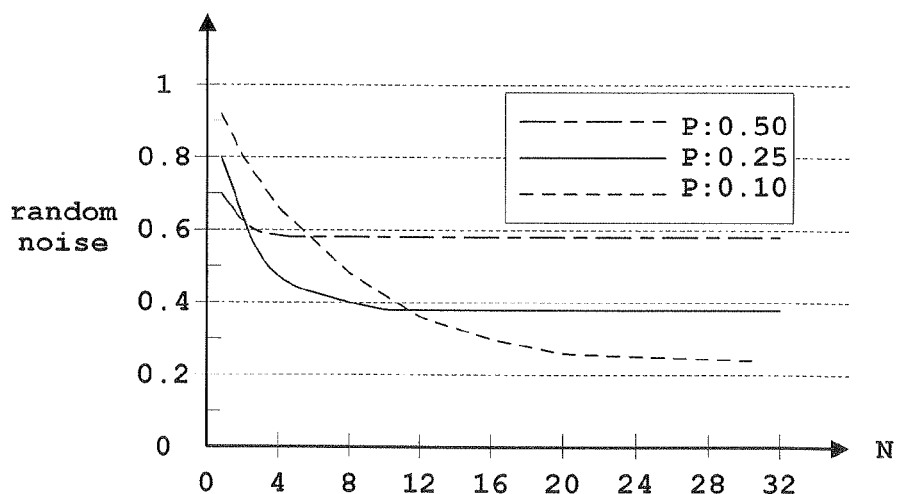
[FIG. 13]Schematic view showing variations of random noise occurring with the frequency of recursive computation when load ratios are changed in the third embodiment.

In Embodiment 3, the lag image is obtained by recursive process (see equation (3) above) which is a recursive weighted average as recursive computation, which realizes a lag correction with increased reliability. Regarding the S/N ratio, as shown in FIG. 13, when the load ratio P in equation (3) above is 0.25 (see the solid line in FIG. 13) the random noise components are reduced to 0.39 by repeating the recursive computation eight times or more. The random noise components of X-ray image Y after the lag correction cause a deterioration not exceeding 7% which is almost the same as the 6% in Embodiment 2 described hereinbefore where the lag image is obtained by directly using eight X-ray detection signals. Thus, the lag correction can be effected without lowering the S/N ratio.

This invention is not limited to the foregoing embodiments, but may be modified as follows:

(1) In each embodiment described above, a fluoroscopic apparatus as shown in FIG. 1 has been described by way of example. This invention may be applied also to a fluoroscopic apparatus mounted on a C-shaped arm, for example. This invention may be applied also to an X-ray CT apparatus. This invention is useful particularly when actual photography (rather than fluoroscopy) is carried out as by an X-ray radiographic apparatus.

(2) In each embodiment described above, the flat panel X-ray detector (FPD) 3 has been described by way of example. This invention is applicable to any X-ray detectors in wide use.

(3) In each embodiment described above, the X-ray detector for detecting X rays has been described by way of example. This invention is not limited to a particular type of radiation detector which may, for example, be a gamma-ray detector for detecting gamma rays emitted from a patient dosed with radioisotope (RI), such as in an ECT (Emission Computed Tomography) apparatus. Similarly, this invention is applicable to any imaging apparatus that detects radiation, as exemplified by the ECT apparatus noted, above.

(4) In each embodiment described above, the FPD 3 is a direct conversion type detector with a radiation (X rays in the embodiments) sensitive semiconductor for converting incident radiation directly into charge signals. Instead of the radiation sensitive type, the detector may be the indirect conversion type with a light sensitive semiconductor and a scintillator, in which incident radiation is converted. Into light by the scintillator, and the light is converted into charge signals by the light sensitive semiconductor.

(5) In each embodiment described above, an operation is started to acquire X-ray detection signals in time of non-irradiation after lapse of the predetermined time (i.e. the waiting time $T_W$ in each embodiment) from X-ray irradiation in a preceding imaging event. Where the short and medium time constant, components are at a negligible level, the acquisition of X-ray detection signals may be started simultaneously with a transition from the X-ray irradiation in the preceding imaging event to the non-irradiation state. This applies also to radiation other than X rays.

(6) In each embodiment described above, the lag image serving as the basis for the lag correction includes data of X-ray detection signal $I_N$ acquired immediately before a start of X-ray irradiation in the current imaging event. It is not absolutely necessary to include the data of X-ray detection signal $I_N$. However, since the latest data is the most reliable, it is desirable, as in each embodiment, to obtain a lag image including the data of X-ray detection signal $I_N$, and perform the lag correction by removing lags using the lag image. This applies also to radiation other than X rays.

(7) In each embodiment described above, based on both the offset image and gain correcting image, a lag image and an X-ray image are acquired taking both images into consideration. Instead, based only on one of the offset image and gain correcting image, a lag image and an X-ray image may be acquired taking only one of the images into consideration. This applies also to radiation other than X rays.

(8) In each embodiment described above, in order to take the offset image and gain correcting image into consideration, equation (1) above is used for deriving the lag image, and equation (2) above is used for deriving the X-ray image. A technique of taking the offset image and gain correcting image into consideration in a usual method is not limited to the subtraction or division as in equation (1) or (2) above.

(9) Embodiment 3 described above employs the recursive weighted, average (recursive process) as shown in the foregoing equation (3). The recursive computation is not limited to the recursive weighted average, but may be an inveighed recursive computation. Thus, function $f(I_N, L_{N-1})$ expressed by X-ray detection signal $I_N$ and lag image $L_{N-1}$ may be expressed by the lag image $L_N$ to serve the purpose.

INDUSTRIAL UTILITY

As described above, this invention is suited to a radiographic apparatus having a flat panel. X-ray detector (FPD).

The invention claimed is:

1. A radiographic apparatus for obtaining radiographic images based on radiation detection signals, comprising:
   a radiation emitting device for emitting radiation toward an object under examination;
   a radiation detecting device for detecting radiation transmitted through the object;
   an offset image storage device for storing offset images corresponding to a plurality of storage times for accumulating information on signals, the offset images being used to perform offset correction for removing offset values superimposed on the signals;
   a non-irradiation signal acquiring device for acquiring a plurality of radiation detection signals detected from the radiation detecting device in time of non-irradiation before irradiation of the radiation in an imaging event;
   a lag image acquiring device for acquiring a lag image based on the plurality of radiation detection signals acquired by the non-irradiation signal acquiring device, and the offset images stored in said offset image storage device and corresponding to storage times for the non-irradiation signal acquiring device;
   an irradiation signal acquiring device for acquiring radiation detection signals detected from the radiation detecting device in time of irradiation of the radiation in the imaging event;
   a radiographic image acquiring device for acquiring a radiographic image based on the radiation detection signals acquired by the irradiation signal acquiring device, and the offset images stored in said offset image storage device and corresponding to the storage times for the irradiation signal acquiring device; and
   a lag correcting device for removing lags, using the lag image acquired by said lag image acquiring device, from the radiographic image acquired by the radiographic image acquiring device, thereby performing a lag correction of lag-behind parts by removing the lag-behind parts from the radiation detection signals.

2. A radiographic apparatus for obtaining radiographic images based on radiation detection signals, comprising:
   a radiation emitting device for emitting radiation toward an object under examination;
   a radiation detecting device for detecting radiation transmitted through the object;
   a gain correcting image storage device for storing gain correcting images corresponding to a plurality of storage times for accumulating information on signals, the gain correcting images being used to perform gain correction for equalizing signal levels of pixels to be outputted;
   a non-irradiation signal acquiring device for acquiring a plurality of radiation detection signals detected from the radiation detecting device in time of non-irradiation before irradiation of the radiation in an imaging event;
   a lag image acquiring device for acquiring a lag image based on the plurality of radiation detection signals acquired by the non-irradiation signal acquiring device, and the gain correcting images stored in said gain correcting image storage device and corresponding to storage times for the non-irradiation signal acquiring device;
   an irradiation signal acquiring device for acquiring radiation detection signals detected from the radiation detecting device in time of irradiation of the radiation in the imaging event;
   a radiographic image acquiring device for acquiring a radiographic image based on the radiation detection signals acquired by the irradiation signal acquiring device, and the gain correcting images stored in said gain correcting image storage device and corresponding to the storage times for the irradiation signal acquiring device; and
   a lag correcting device for removing lags, using the lag image acquired by said lag image acquiring device, from the radiographic image acquired by the radiographic image acquiring device, thereby performing a lag correction of lag-behind parts by removing the lag-behind parts from the radiation detection signals.

3. A radiation detection signal processing method for performing a signal processing to obtain radiographic images based on radiation detection signals detected by irradiating an object under examination, said signal processing comprising:
   an offset image storing step for storing, before an imaging event, offset images corresponding to a plurality of storage times for accumulating information on signals, the offset images being used to perform offset correction for removing offset values superimposed on the signals;
   a non-irradiation signal acquiring step for acquiring a plurality of radiation detection signals in time of non-irradiation before irradiation of the radiation in the imaging event;
   a lag image acquiring step for acquiring a lag image based on the plurality of radiation detection signals acquired in the non-irradiation signal acquiring step, and the offset images stored in said offset image storage step and corresponding to storage times in the non-irradiation signal acquiring step;

an irradiation signal acquiring step for acquiring radiation detection signals in time of irradiation of the radiation in the imaging event;

a radiographic image acquiring step for acquiring a radiographic image based on the radiation detection signals acquired in the irradiation signal acquiring step, and the offset images stored in said offset image storage step and corresponding to the storage times in the irradiation signal acquiring step; and a lag correcting step for removing lags, using the lag image acquired in said lag image acquiring step, from the radiographic image acquired in the radiographic image acquiring step, thereby performing a lag correction of lag-behind parts by removing the lag-behind parts from the radiation detection signals.

4. A radiation detection signal processing method for performing a signal processing to obtain radiographic images based on radiation detection signals detected by irradiating an object under examination, said signal processing comprising:

a gain correcting image storing step for storing, before an imaging event, gain correcting images corresponding to a plurality of storage times for accumulating information on signals, the gain correcting images being used to perform gain correction for equalizing signal levels of pixels to be outputted;

a non-irradiation signal acquiring step for acquiring a plurality of radiation detection signals in time of non-irradiation before irradiation of the radiation in the imaging event;

a lag image acquiring step for acquiring a lag image based on the plurality of radiation detection signals acquired in the non-irradiation signal acquiring step, and the gain correcting images stored in said gain correcting image storage step and corresponding to storage times in the non-irradiation signal acquiring step;

an irradiation signal acquiring step for acquiring radiation detection signals in time of irradiation of the radiation in the imaging event;

a radiographic image acquiring step for acquiring a radiographic image based on the radiation detection signals acquired in the irradiation signal acquiring step, and the gain correcting images stored in said gain correcting image storage step and corresponding to the storage times in the irradiation signal acquiring step; and a lag correcting step for removing lags, using the lag image acquired in said lag image acquiring step, from the radiographic image acquired in the radiographic image acquiring step, thereby performing a lag correction of lag-behind parts by removing the lag-behind parts from the radiation detection signals.

* * * * *